United States Patent [19]

Goverde et al.

[11] 4,211,530

[45] Jul. 8, 1980

[54] TEST-KIT AND METHOD FOR THE ESTIMATION OF LP-X

[75] Inventors: Bastiaan C. Goverde; Peter S. L. Janssen, both of Oss, Netherlands; Gerhard M. Kostner, Graz, Austria

[73] Assignee: Akzo N.V., Arnhem, Netherlands

[21] Appl. No.: 876,133

[22] Filed: Feb. 8, 1978

[30] Foreign Application Priority Data

Feb. 18, 1977 [NL] Netherlands .......................... 7701800

[51] Int. Cl.² ............................................. G01N 33/16
[52] U.S. Cl. ................................... 23/230 B; 23/909; 23/915; 206/569; 422/61; 424/12
[58] Field of Search ............................ 424/12; 422/61; 23/230 B, 61

[56] References Cited

U.S. PATENT DOCUMENTS

| | | | |
|---|---|---|---|
| 3,954,409 | 5/1976 | Hsia | 23/230 B |
| 4,045,176 | 8/1977 | Proksch | 23/230 B |
| 4,126,416 | 11/1978 | Sears | 23/230 B |

OTHER PUBLICATIONS

Chemical Abstracts, 81:87359t (1974).
C. C. Heuck et al., Clin. Chem. 23(3), 536–540 (1977).
G. M. Kostner et al., Clin. Chem. 20(6), 676–681 (1974).

*Primary Examiner*—Sidney Marantz
*Attorney, Agent, or Firm*—Stevens, Davis, Miller & Mosher

[57] ABSTRACT

A diagnostic method and test-kits for the demonstration and determination of the lipoprotein LP-X in serum by removal of interfering lipoproteins, precipitation of LP-X in the remaining serum and measuring the LP-X content in the suspension, obtained by photo-optical or visual methods.

10 Claims, No Drawings

TEST-KIT AND METHOD FOR THE ESTIMATION OF LP-X

The invention relates to a method for the demonstration and estimation of the so-called lipoprotein-X (LP-X) and to a test-kit for use in this method.

Serum contains a number of "normal" lipoproteins, which, classified by density, are designated as chylomicrons, VLDL, LDL and HDL. They contain free and esterified cholesterol, triglycerides, phospholipids and proteins.

In some disease conditions, other types of lipoprotein may be formed in serum and these can be considered as "abnormal" lipoproteins. The LP-X is one of these abnormal lipoproteins. With the diagnostic aids now available, LP-X or a lipoprotein related to LP-X can be demonstrated in a disease based on a deficiency of the enzyme lecithin:cholesterol acyltransferase (EC 2.3.1.43) in the liver, an extremely rare inborn error of metabolism. The inability of the liver to esterify cholesterol is considered to be one of the reasons why LP-X, a lipoprotein with a relatively high content of free cholesterol, is formed. LP-X, or a substance resembling LP-X very closely, is also found in some children shortly after birth, a finding which can, for example, be attributed to physiological immaturity of hepatic function during the initial period of the child's life, or to the physiological marked reduction in synthesis of bile acids, as a result of which the absorption of fat in the young infant is also reduced. In this case LP-X only appears post-natally, after ingestion of food has commenced.

LP-X also occurs in the blood in almost all patients suffering from cholestasis. As a result of an intra- or extra-hepatic occlusion, a number of pathological changes occur, for example, bilirubin metabolism changes so that the patients become jaundiced. The activities of a number of enzymes in the blood, e.g. alkaline phosphates (EC 3.1.3.1), D-glutamyl-transferase (EC 2.3.2.1) and other serum aminotransferases (EC 2.6.1.2 and/or 2.6.1.6), may furthermore also change. Jaundice may however also be caused by many other disease states, while these disorders may also exert their influence on the abovenoted enzyme activities. It is therefore universally recognised that LP-X is a much more specific parameter for the existence of cholestasis than are the abovenoted parameters. It is not without cause that LP-X is also called a "cholestasis specific lipoprotein".

Most methods of determining LP-X are based on the observation that in agar gel electrophoresis LP-X migrates to the cathode, i.e. in the opposite direction than the other lipoproteins. Identification with the aid of, for example, certain lipophilic dyes, immune precipitants against LP-X or precipitating polyvalent anions render qualitative determination possible, and even in extreme cases a semi-quantitative determination. This quantification may be optionally further improved by other techniques for determination and identification, such as the use of radio-active labelled compounds or cutting out the agar gel containing the LP-X fraction and determining chemically certain constituents such as, for example, the phospholipids. The electrophoretic technique in all these cases requires much time and expertise, while the degree of difficulty is very great. The results are sometimes very unreliable, for example after incorrect handling and storage of the sample to be analysed, or on use of an unsuitable or old agar.

There are also a number of quantitative immunochemical techniques, in which, for example, the serum, after removal of interfering lipoproteins, is subjected to techniques such as radial diffusion according to Mancini or to electro-immunodiffusion according to Laurell e.g. as described in Clin.Chem. 1974, 20(6), 676-81. In these cases a more accurate determination of the LP-X is certainly possible, but the techniques require time-consuming preparation, and it still costs several hours, or in a few cases even days, before the result can be read. The benefit of an accurate quantitative method of determination for LP-X is exceptionally great. If this meets the stringent requirements with respect to simplicity, rapidity and reproducibility, the LP-X level can be used as a guide in the diagnosis and therapy of cholestasis. If the increase remains below a borderline value of about 400 mg per 100 ml, then the condition concerned is in many cases an intra-hepatic cholestasis, while in extra-hepatic cholestasis, which is generally operable, the serum LP-X level may increase too far above this value. A quantitative test for LP-X also makes a valuable contribution to the diagnosis and the recovery process in cases of cholestasis which are caused by the use of certain medicaments.

A method for the qualitative and quantitative determination of LP-X has now been found; the said method consists of first removing the apo-B-containing lipoproteins in ways which are in themselves known, after which substances which lower the solubility of lipoproteins are added to the residual serum and the amount of LP-X in the resultant LP-X suspension is measured and determined with the aid of photo-optical methods.

The removal of the interfering lipoproteins is preferably achieved by bringing the serum into contact with an antibody or antiserum directed against the low density lipoprotein (LDL) or against the apoprotein-B thereof. This antiserum or antibody is preferably kept and added in a freeze-dried state. It may also be used in the form of a solution.

Apart from an immunochemical separation, the interfering lipoproteins may also be removed by addition of certain substances such as concanavalin A or other lectins, hydroxyl apatite, aerosil, etc.

Antibodies against lipoproteins containing apo-B may be obtained from mammals, for example the rabbit, cow, sheep or horse, by immunizing these with lipoproteins or delipidized lipoproteins of human origin which contain apolipoprotein B, for example human LDL. The antisera obtained in this way might be processed in order to obtain (a) lipoprotein-free animal sera, (b) the gamma-globulin fraction of it, or (c) the pure antibody mono-specific for LP-B.

It was found that sera containing LP-X, brought into contact with solutions of anti-lipoprotein B or lyophilized anti-lipoprotein B, give a precipitate which removes all VLDL and LDL (with the exception of LP-X). Surprisingly, it proved that this precipitation occurs practically instantaneously, and that after separation of the agglutinate formed, e.g. by filtration or centrifugation, a clear solution is immediately obtained. If the amount of antibody present is insufficient to bind all the VLDL and LDL in the sample, the filtrate is turbid or opaque. In that case, a further amount of the antibody is added to the serum, after which the sample is filtered or centrifuged again. In all cases, the LP-X in the residual serum remains in solution, together with the HDL in as far as this consists of particles with the apolipoproteins A and C.

After separation of the interfering lipoproteins, optionally as immune-complex, the substances for reducing the solubility of LP-X are added to the residual serum. This can be achieved by adding to the serum substances with an anionic or polyanionic character, such as salts of tungstic acid; phosphotungstic acid; molydenic acid; salts of higher aliphatic sulphates and carboxylic acids such as sodium dodecyl sulphate, sodium laurate and sodium oleate; salts of cholic acids such as sodium cholate or potassium desoxycholate; polycations, sulphated polysaccharides such as dextran sulphate and heparinoids.

The named anionic reagents are preferably used in combination with metal compounds, particularly divalent metal compounds such as salts of magnesium, calcium and manganese. Use may also be made of, for example, polyvinylpyrrolidone.

The addition of the reagents named in the preceding paragraph renders the LP-X insoluble or poorly soluble. In general, these substances are added in such concentrations that a system of fine particles, as homogenously dispersed as possible, is formed, such that the insoluble system settles only very slowly. The quantity of LP-X is subsequently determined by means of photo-optical methods, for example by turbidometry or nephelometry. This is achieved by measurement in a turbidometer or nephelometer, according to the following principle. When light falls on a suspended system of fine particles, part of the incident light is transmitted, a further part is scattered and a part will possibly also be absorbed. In turbidometry, the ratio of the transmitted light to the incident light is used to determine the concentration of the suspended particles. In nephelometry, the ratio of the scattered light to the incident light is used for this determination of concentration.

Standardization is achieved by reference to purified LP-X isolated from the blood of cholestatic patients or animals artificially rendered cholestatic (e.g. a dog). Since LP-X cannot be made available on a large scale, and furthermore has only limited keeping qualities even with the best possible stabilization, an internal turbidometric or nephelometric standard can be introduced. This preferably consists of a lyophilisate, prepared from a serum of human or animal origin, or of substances which just as LP-X give a homogenously dispersed system of particles with the anion reagent used. Examples of this are lyophilized or stabilized solutions of human or animal lipoproteins such as VLDL and/or LDL, lyophilized or dissolved protamine sulphate or a mixture thereof. In this case, the internal standard is calibrated with reference to LP-X, which considerably reduces the requirement for this expensive material without detracting from the so essential reliability.

Although a number of elements in this test method are in themselves matters of common knowledge, when integrated into the method as a whole they provide a new and surprisingly rapid, simple and specific test possessed of a very high degree of reliability. The application moreover does not necessitate the use of expensive and specific equipment, nor does it require great expertise. On the contrary, the test can be performed by relatively untrained personnel with conventional laboratory equipment.

The test-kit, to be used in the method according to the invention, consists in essence of:

(a) an antiserum or antibody directed against apolipoprotein B;
(b) a LP-X standard and/or a turbidity standard calibrated against LP-X;
(c) an aqueous reagent which reduces the solubility of LP-X.

The immunological component named in (a) may optionally be coupled to an insoluble carrier so that lipoproteins interfering with the determination may be more readily removed from the serum.

The invention is further illustrated by means of the following examples.

EXAMPLE I

Test-kit comprising:
10 reagent tubes $R_1$ closed with rubber stoppers, containing 5 mg lyophilized anti-apolipoprotein B each, prepared according to Biochem. Biophys. Acta, 188 (1969), 157, from the serum of horses immunized with pure human LDL;
10 identical reagent tubes $R_2$ containing 0.1 mg protamine sulfate in a lyophilized state;
$2 \times 10$ identical reagent tubes labeled $R_{3a}$ and $R_{3b}$ respectively, clean without stoppers;
1 vial containing stabilised LP-X positive serum with a known content of LP-X (103,3 mg/100 ml);
1 vial containing 1 ml of an aqueous solution (precipitating reagent P) of:

dextran sulphate 500, sodium salt: 0.65 mg
magnesium chloride hexahydrate: 12.7 mg
Nipagin: 1 mg
Nipasol: 1 mg 1 vial containing 10 ml of an aqueous solution (diluent D) of:

sodium chloride: 90 mg
magnesium chloride hexahydrate: 100 mg

EXAMPLE II

The following components of the test-kit described in example I are placed in a rack:
2 tubes $R_1$
1 tube $R_2$
2 tubes $R_{3a}$
2 tubes $R_{3b}$ The stoppers are removed from the tubes, after which 150 μl chylomicron-free patients serum is introduced in one tube $R_1$, and 150 μl of the LP-X positive reference serum into another tube $R_1$ and vigorously shaken. These tubes are subsequently centrifuged at 3000 g, after which 50 μl of the clear supernatant is pipetted into each of the tubes $R_{3a}$ and $R_{3b}$. 50 μl of physiological saline is then pipetted into one of the tubes $R_2$.

10 μl dextran sulphate solution is then pipetted into the tubes $R_2$ and $R_{3b}$. Finally, 500 μl of the diluent (D) is introduced into tubes $R_2$, $R_{3a}$ and $R_{3b}$.

After vigorous shaking, the tubes are measured in a Zeiss PMQ II spectrophotometer at 400 nanometers. Physiological saline serves for setting the zero point for sample $R_2$ and the content of the tubes $R_{3a}$ serves for setting the zero point for the samples in tubes $R_{3b}$ (for each sample individually).

The absorptions measured are:
$R_2$: 0.140
$R_{3b}$: (patients serum): 0.620
$R_{3b}$: (LP-X standard serum): 0.450.

From these absorptions it can be calculated that the LP-X content of the serum of the patient is $142.3 \pm 5.7$ mg/100 ml. An absorption of 0.100 for the turbidity standard protamine sulphate is equivalent to 22.95 mg LP-X/100 ml.

EXAMPLE III

A test-kit as in Example I is assembled whereby the vial with the LP-X standard is omitted, and the lyophilized anti-apolipoprotein B in the tubes $R_1$ is replaced by 50 µl of a solution of 3 mg anti-apolipoprotein B from the rabbit.

A determination is performed with another patients serum in complete accordance with example II (with omission of the LP-X reference). The turbidity measurement of tube $R_{3b}$ gives a value of 0.285. The LP-X content of this serum can be calculated as 87.2±3.5 mg per 100 ml.

EXAMPLE IV

A test-kit as in example I is assembled with the following modifications:
 (a) the vial with the reference LP-X is replaced by a vial containing lyophilized horse serum; this has to be solubilized before use by the addition of 1 ml of saline;
 (b) the anion reagent consists of 1 ml of an aqueous solution of:
heparin (150 USP/mg): 6 mg
MnIIchloride tetrahydrate: 60 mg
Nipagin: 1 mg
Nipasol: 1 mg
 (c) the diluent consists of 10 ml of an aqueous solution of
sodium chloride: 90 mg
MnIIchloride tetrahydrate: 100 mg The sera from three patients are examined in complete accordance with the prescription in example II. The measured absorptions are:

| sample 1 | sample 2 | sample 3 |
|---|---|---|
| $R_2$ : 0.425 | $R_2$ : 0.434 | $R_2$ : 0.418 |
| $R_{3b}$ : (LP-X standard) 0.652 | | |
| $R_{3b}$ : 0.825 | $R_{3b}$ : 0.072 | $R_{3b}$ : 0.008 |

From these measurements it may be concluded or calculated respectively that sample 1 contains 140.2±4.9 mg/100 ml of LP-X. Sample 2 contains 12.0±0.4 mg LP-X/100 ml. Sample 3 does not contain a measurable amount of LP-X. The total duration of the assay of these three samples was 21 minutes.

EXAMPLE V

A test-kit as in example I is assembled whereby the following components have been changed:
 (a) the vial with the "LP-X standard" contains a stabilized solution with 100 mg/100 ml human LDL;
 (b) the reagent for the turbidity is composed of:
sodium phosphotungstate: 10 mg
magnesium chloride hexahydrate: 50 mg
water: to 1 ml
 (c) the vial with the diluent is composed of:
sodium chloride: 90 mg
$MgCl_2.6H_2O$: 160 mg
water: to 10 ml The turbidity of the samples in this case is measured with a laser nephelometer (Behring Werke A.G., He-Ne Laser).

Because of the higher sensitivity, all samples in this case are diluted by addition of 1 ml of solution D instead of 0.5 ml.

The measured values are:

| sample 1 | sample 2 |
|---|---|
| $R_2$ : 6.29 V | $R_2$ : 6.33 V |
| $R_{3b}$ (standard LDL) 9.61 V | |
| $R_{3b}$ : 11.62 V | $R_{3b}$ : 1.45 V |

From these values it has been calculated that sample 1 contains 103.2±3.1 mg LP-X/100 ml and sample 2 12.8±0.35 mg/100 ml. The assumed LP-X content of the protamine sulphate standard is 55.8 mg/100 ml and of the LDL standard is 85.3 mg/100 ml.

EXAMPLE VI

Test-kit as in example V in which the turbidity reagent is composed of:
sodium dodecyl sulphate: 14 mg
water: to 1 ml The diluent consists of:
sodium chloride: 90 mg
$MgCl_2.6H_2O$: 124 mg
water: to 10 ml

EXAMPLE VII

Test-kit comprising 30 reagent tubes $R_1$ closed with rubber stoppers containing 2 mg lyophilized anti-apolipoprotein B prepared according to Biochem. Biophys. Acta 188 (1969) 157, from the serum of sheep immunized with pure human LP-B.
 1 black plastic or glass tray with bore holes closed at the bottom.
 1 vial containing 1 ml of an aqueous solution of:
sodium phosphotungstate: 10 mg
$MgCl_2.6H_2O$: 50 mg
Nipagin: 1 mg
Nipasol: 1 mg
 1 Pasteur pipette
 1 vial containing stabilized LP-X positive serum.
 1 vial containing stabilized LP-X negative serum.

PROCEDURE

The stoppers are removed from the tubes and 50 µl of different samples as well as of the positive and negative standard are pipetted into individual tubes $R_1$. The vials are vigorously shaken and allowed to stand for 5 minutes at room temperature. Then the tubes are centrifuged at 3000 g for 5 minutes. The supernatant of the tubes are poored directly into individual holes of the plastic tray after which one drop of the precipitating agent is added.

The immediate appearance of a precipitate or of a turbidity is indicative for LP-X.

We claim:
1. A method for the demonstration and determination of the lipoprotein LP-X in serum, comprising
  initially removing the interfering apo-B-containing lipoproteins from serum,
  subsequently adding to the remaining serum substances that reduce the solubility of lipoproteins, thus forming a suspension of LP-X, and
  measuring and determining the amount of LP-X by visual or photo-optical methods.
2. The method according to claim 1, comprising added as solubility-reducing compound a material se- lected from the group consisting of a (poly)anion reagent and a (poly)cation reagent.

3. The method according to claim 1, comprising adding a (poly)anion reagent as solubility-reducing compound.

4. The method according to claim 1, comprising adding an antibody or antiserum directed against the lipoprotein LDL or against the apoprotein-B thereof to said serum for removal of the interfering lipoproteins.

5. The method according to claim 4, comprising adding said antiserum or antibody in a freeze-dried state.

6. A test-kit, for use in the method according to any one of claims 1, 3, 4 or 5, consisting essentially of:

(a) an antiserum or antibody directed against apolipoprotein B;
(b) a LP-X standard, and/or a turbidity standard calibrated against LP-X; and
(c) a reagent that reduces the solubility of LP-X.

7. The test-kit according to claim 6, wherein said antiserum or antibody specified under (a) is coupled to a solid carrier.

8. The test-kit according to claim 6, wherein said LP-X specified under (b) is of animal origin.

9. The test-kit according to claim 6, wherein said turbidity standard specified under (b) contains protamine sulphate.

10. The test-kit according to claim 6, wherein said reagent (c) also contains a multivalent metal compound.

* * * * *